United States Patent [19]

Graciotti et al.

[11] Patent Number: 4,713,779
[45] Date of Patent: Dec. 15, 1987

[54] VIDEO CONVERTER

[75] Inventors: Alessandro Graciotti, Cupertino; Herbert A. Kutscha, Los Gatos, both of Calif.

[73] Assignee: Ing.C. Olivetti & Co. S.p.A., Invrea, Italy

[21] Appl. No.: 709,442

[22] Filed: Mar. 8, 1985

[51] Int. Cl.⁴ .................... G06F 15/68; H04N 5/14
[52] U.S. Cl. ..................... 364/521; 340/723; 358/166; 364/518
[58] Field of Search .............. 364/521, 710, 723; 340/723, 728, 347 DD; 358/166, 284, 160

[56] References Cited

U.S. PATENT DOCUMENTS

| | | | |
|---|---|---|---|
| 3,983,328 | 9/1976 | Newell | 358/160 |
| 4,238,774 | 12/1980 | Lehman | 340/728 X |
| 4,309,700 | 1/1982 | Kraemer | 340/723 X |
| 4,437,122 | 3/1984 | Walsh et al. | 358/166 |
| 4,439,762 | 3/1984 | Van Vliet et al. | 340/728 X |
| 4,528,561 | 7/1985 | Kitamura | 340/728 X |

*Primary Examiner*—Errol A. Krass
*Assistant Examiner*—Kevin J. Teska
*Attorney, Agent, or Firm*—Darby & Darby

[57] ABSTRACT

A device for converting display parameters adapted for use with a personal computer having a display defined by a first set of parameters to a display having a second set of parameters. The converter includes a latch for storing data received from the microcomputer data bus that is indicative of the parameter to be controlled and a read only memory coupled to the latch and also coupled to the data bus. The read only memory will select a new value corresponding to the parameter to be converted from data received from the latch and the parameter data received from the data bus.

12 Claims, 2 Drawing Figures

VIDEO CONVERTER

BACKGROUND OF THE INVENTION

1. Field of the Invention

The subject invention pertains to the field of video displays and more particularly to a device that provides compatibility between a computer adapted for use with a first video display format defined by a first set of parameters and software originally designed for use with a computer having a second video format defined by a second set of parameters.

2. Description of the Prior Art

A wide variety of computers and particularly personal computers have been introduced over the past several years. Of the many that have been sold and manufactured, several have emerged as defacto standards due to their very large popularity. The high popularity of particular computers has in turn encouraged various third party software vendors to write many programs adapted to the popular machines.

Heretofore, computer manufacturers have had to decide whether to design a totally new machine having new and improved features while sacrificing some or all compatibility with the many software packages designed for a standard machine or to design essentially a copy of the standard machine, capable of running most if not all of the software previously designed for the standard machine. If the choice was made for compatibility, the resulting computer generally had few if any advantages or improved capabilities over the machine which it emulated.

Recently, computer users have demanded improved graphic capabilities in their machines to provide for more readable, informative and eye catching displays. The improved displays make better presentations of data and decrease eye strain. The improved displays thus encourage the use of a particular vendor's software as well as the particular computer with which the software is used. Therefore, one area in which manufacturers have striven to make improvements is in the computer display. The displays used with most computers are cathode-ray tube (CRT) based. Their resolution is usually specified in the number of vertical and horizontal pixels (dots or picture units) that they can distinctly display.

One personal computer that has enjoyed a large degree of consumer acceptance and therefore has had a large quantity software written for it is the IBM PC, manufactured by International Business Machines Corp., Armonk, N.Y. Due to the tremendous acceptance of the IBM PC, particularly by commercial users, many manufacturers have found it desirable to design a computer compatible with the IBM Pc yet have striven to improve the machine in several areas. One such area is in its display.

The IBM PC uses a display that can show 640×200 pixels. This has been shown to be just barely adequate for office graphics. Further, this machine, like others, displays a character formed from a matrix of 8×8 pixels. In order to obtain letters having true descenders and yet still have sufficient space between consecutive lines of text on the display, it is necessary, when using a 8×8 letter, to use a very small, low resolution letter since in order to provide for the true descenders, less than the full 8×8 pixel matrix is used.

It is thus preferable to use a pixel matrix for each character having more than 8×8 pixels. One such matrix that may be used is an 8×16 matrix having 8 pixels in the horizontal direction and 16 pixels in the vertical direction. As will be clear to those skilled in the art, such a matrix can retain compatibility with an 8×8 pixel matrix merely by scanning consecutive pairs of rows identically.

Most personal computer display screens use an 80×25 character screen. That is, up to 80 columns of characters and 25 lines or rows of characters can be displayed on a screen.

For 8×8 characters, 640×200 pixels can be displayed on the screen. To use an 8×16 character, the computer must be capable of displaying 640×400 pixels.

Generally, there are 3 levels of interface with a computer's display circuitry. These are (1) hardware, (2) the computer's basic input/output system and (3) the computer's operating system.

In a machine such as the IBM PC, the operating system does not support all screen functions well. It does not allow instructions to the screen since once the screen parameters are set they usually cannot be reset. Consequently, much software writes directly to the hardware or to the basic input/output system and bypasses the operating system.

While a program which utilizes only the operating system in order to write to the computer screen would be usable with a compatible machine having a higher resolution, any program that directly programmed the hardware would show a scrambled display.

Heretofore, a manufacturer of a computer who wished to make a product compatible with software designed for an IBM PC and its standard 640×200 pixel screen had to sacrifice a degree of compatibility if he used a higher resolution screen. Typically, manufacturers of such compatible computers would just simply choose to forego the advantages offerred by a higher resolution screen in order to maintain compatibility.

It is thus an object of the present invention to provide a device which permits the use of software designed for a standard computer having a relatively low resolution screen with another computer having a higher resolution screen.

It is a further object of the invention to provide a device which permits the use of the higher resolution screen with software designed for it, yet still remain completely compatible with software requiring a lower resolution screen.

It is still another object to provide a personal computer having finely detailed characters when used with software operating from the computer operating system.

These and other objects of the invention will be more apparent upon reference to the following specification and the annexed drawings.

SUMMARY OF THE INVENTION

In accordance with an illustrative embodiment demonstrating objects and features of the present invention, there is provided a device for converting video display data adapted for a display having a first format to a display having a second format where the display control device has an address register and a plurality of control registers. The display controller defines and controls the display format. Address register data is stored, and applied along with sequentially received control register data to a memory. The memory reads out the data addressed by the address register and control register addresses to look up a new value from tables stored within the memory, to be used with the display having the second format.

DETAILED DESCRIPTION OF THE PREFERRED EMBODIMENTS

Figure 1:
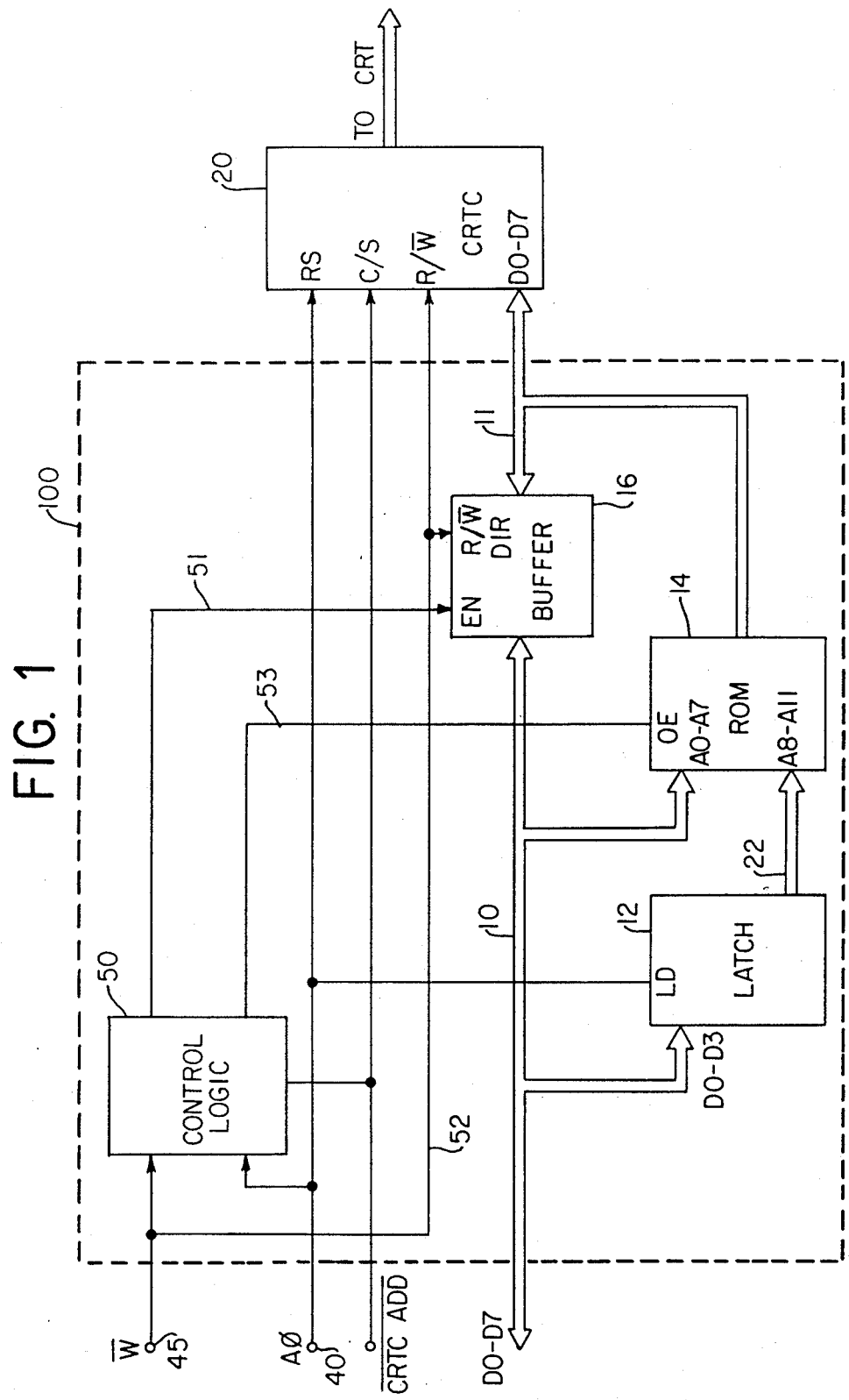
FIG. 1 is an overall block diagram of the device according to the present invention.

FIG. 1 shows a block diagram of the video computer 100 according to the present invention. It functions to convert, on the fly, CRT display parameters used with industry standard machines to those required in a computer using a different display having different parameters. The display parameters include, for example, the horizontal vertical sync positions and widths, number of characters displayed.

Input data D0–D7 which provides data with respect to the display parameters, may be provided by software written for the standard machine and is applied on internal data bus 10. This data is supplied in parallel to latch 12, ROM 14 and buffer 16. Data from buffer 16 and ROM 14 may then be applied to CRT controller data bus 11 and in turn applied to the CRT controller (CRTC) 20.

CRT controller 20 generates a raster scan displayed on a CRT. A widely used CRT controller is the 6845 which is manufactured by for example Motorola Inc., 5005 East McDowell Road, Phoenix, Ariz. 85008.

The 6845 has 19 accessible internal registers, which are used to define and control the raster scanned CRT display. One of these registers, the index or address register, is actually used as a pointer to the other 18 registers. It is a write-only register which is loaded from the microprocessor by executing the appropriate instruction received from data bus 10. The 5 least significant bits of the bus (D0–D4) are then loaded into the index register.

In order to load any of the other 18 registers, the index register is first loaded with the necessary pointer, then the data register is loaded with the information to be placed in the selected register. The 6845 may be considered a two register device. The first, known as the address or pointer register is called when A0=0. The signal A0 is received at terminal 40 and applied to the RS (register select) terminal of the CRTC 20. If A0=1 the value of the display parameter desired is placed into the register selected by the address in the pointer register. These addresses are received from the software or operating system. These values, in a device such as the IBM PC will be fed directly or through a buffer to the 6845.

Table 1 defines the values that must be loaded into the 6845 CRT controller register to control various different modes of operation.

TABLE I

| Address Register | Register Number | Register Type | Units | I/O | 40 by 25 Alphanumeric | 80 by 25 Alphanumeric | Graphic Modes |
|---|---|---|---|---|---|---|---|
| 0 | R0 | Horizontal Total | Character | Write Only | 38 | 71 | 38 |
| 1 | R1 | Horizontal Displayed | Character | Write Only | 28 | 50 | 28 |
| 2 | R2 | Horizontal Sync Position | Character | Write Only | 2D | 5A | 2D |
| 3 | R3 | Horizontal Sync Width | Character | Write Only | 0A | 0A | 0A |
| 4 | R4 | Vertical Total | Character Row | Write Only | 1F | 1F | 7F |
| 5 | R5 | Vertical Total Adjust | Scan Line | Write Only | 06 | 06 | 06 |
| 6 | R6 | Vertical Displayed | Character Row | Write Only | 19 | 19 | 64 |
| 7 | R7 | Vertical Sync Position | Character Row | Write Only | 1C | 1C | 70 |
| 8 | R8 | Interlace Mode | — | Write Only | 02 | 02 | 02 |
| 9 | R9 | Maximum Scan Line Address | Scan Line | Write Only | 07 | 07 | 01 |
| A | R10 | Cursor Start | Scan Line | Write Only | 06 | 06 | 06 |
| B | R11 | Cursor End | — | Write Only | 07 | 07 | 07 |
| C | R12 | Start Address (H) | — | Write Only | 00 | 00 | 00 |
| D | R13 | Start Address (L) | — | Write Only | 00 | 00 | 00 |
| E | R14 | Cursor Address (H) | — | Read/Write | XX | XX | XX |
| F | R15 | Cursor Address (L) | — | Read/Write | XX | XX | XX |
| 10 | R16 | Light Pen (H) | — | Read Only | XX | XX | XX |
| 11 | R17 | Light Pen (L) | — | Read Only | XX | XX | XX |

In operation, signals received from data bus 10 will be translated by a look up table in ROM 14 and the translated values are placed on data bus 11 where they are coupled to CRTC 20. The address of the memory location looked up by ROM 14 consists of 2 parts, the first part A8–A11 is received via bus 22 from latch 12 and the second, A0–A7 is received directly from data bus 10. Latch 12 in turn receives data bits D0–D3 from data bus 10.

In one embodiment of the present invention only data bits D0–D3 are used to select the control register to be selected since the last two address registers indicated on table 1, that is, R16, R17 support a light pen function which is not being used. In this case only registers 0 through 15 are addressed which can be done using only 4 bits, namely bits D0–D3.

Latch 12 will hold the register address received from the processor to select the desired control register to be addressed in the CRTC 20 until the next time the index register is to be rewritten. Latch 12 latches in data bits D0–D3 whenever A0=0. A0=0 only when access to the address register is desired. Bits D0–D3 may then be loaded in simultaneously with the control register data received on data bus 10 which is loaded into ROM 14 address input A0–A7.

Bits D0–D3 are applied to the address bit inputs A8–A11 of ROM 14. Together with bits D0–D7 which are applied to inputs A0–A7 of ROM 14 an 11 bit address is thus constructed, and which address up a location in a look-up table within the ROM. The value stored in the addressed location in the ROM is then placed on data bus 11 and applied to the D0–D7 inputs of CRTC 20.

The invention utilizes a $\overline{\text{CRTCADD}}$ signal which addresses the chip select (C/S) input of CRTC 20. When this signal goes low, the CRTC is selected during CRTC read or write operations.

During operation in the industry standard machine, when the software or hardware requires its CRT controller to perform a function data will be transferred to it in two portions. For the first portion, A0 is set low to indicate that the CRTC address register is being addressed. During this phase of the operation, video converter 100 should remain transparent so that the address register chosen by the software may be routed directly through buffer 16 to the CRT controller 20. Buffer 16 must also be enabled and it receives the appropriate signal on lead 51 at its enable (EN) input from control logic 50. As in the case of many standard buffers known in the art, such as for example a 74LS245, buffer 16 is enabled when the signal received at its enable input terminal EN goes low. During this portion of the operation A0 equals logical zero as received from terminal 40 and is routed both to the control logic 50, latch 12 and to the RS terminal of the CRT controller 20. This signal thus selects the address register and as stated, is also applied to latch 12 which has input terminals coupled to the D0–D3 lines of data bus 10 and will thus load in and present (after being appropriately clocked) D0–D3 on bus 22. Latch 12 holds D0–D3 at its output whenever A0=0 and provides this data to ROM 14 at the A8–A11 inputs.

During the second part of the operation, specific display control data generated from the software may be applied to CRT controller 20. This specific data will, as previously discussed, set the various parameters of the CRT display as detailed in table 1, including for example the number of characters to be displayed in a given row and column as well as sync information, etc. used by a CRT. In the present invention, during this portion of operation, it is now desired to interrupt the signal flow to convert it so that it may be utilized with a microcomputer having a higher resolution than the one for which the program was originally developed.

Buffer 16 is thus disenabled by driving the EN signal from lead 51 high and ROM 14 is enabled by a logical 0 signal received from control logic 50 on lead 53, at its OE (output enable) input terminal. The data now present on data bus 10, that is, data bits D0–D7 represents the specific data which the software program would have ordinarily written to the CRT controller 20 in the standard machine. In the present invention this data instead is applied to the address inputs A0–A7 of ROM 14. As discussed previously, the four most significant bits received at address input terminals A8–A11 will form a first part of an address and the 8 least significant bits will form the second part of the address. ROM 14 has its internal memory organized into 16 tables corresponding to inputs A8–A11 each of which may have up to 256 lines within the table corresponding to address bits A0–A7.

Referring again to Table 1, if the software included a command to change or set the horizontal sync width, for example, it would be necessary to address register No. R3. To do so, the binary number 0011 would be loaded into bits A11, A10, A9 and A8, respectively while A0 is low. This value, which was previously loaded into latch 12 would thereafter cause the ROM to look up values from the horizontal sync width table when A0=1. This value, is ordinarily set to 0A in hexidecimal which corresponds to the time it takes to write 10 characters. If, for example, the higher resolution monitor is using a different sync width, it will look it up in the 0011 table, under the line designated as 0A (location 03 0A) and find a value corresponding to the sync width required by the higher resolution monitor.

As may be noted from table 1, the CRT controller can be written to and also read from. The 6845 CRT controller is only read from for the R14, R15, R16 and R17 registers. Ignoring, for the moment, registers R16 and R17, this means that the cursor position can be read from the CRT controller. To permit reading from CRTC 20 buffer 16 must be bidirectional and have a selectable direction. One such buffer is the 74LS245. In this case, buffer 16 is enabled via a signal on lead 51 from control logic 50 and by a $\overline{W}$ (write) signal on lead 52. When the $\overline{W}$ signal=0, a write operation is designated and the buffer 16 permits the flow of data from the bus 10 to the bus 11. When W=1, a read operation is designated and buffer 16 permits the flow of data from data bus 11 to data bus 10.

During a CRTC 20 read operations, the $\overline{W}$ signal must be high. In this case, the buffer 16 will be enabled and the ROM will be disabled. The direction of data transfer as stated is from data bus 11 to data bus 10 so that the 6845 data bus will communicate directly with the data bus 10, regardless of the status of the signal A0.

During the CRTC 20 address register write operations, both the A0 signal will be low and the $\overline{W}$ signal will be low. In this case, the data bus buffer 16 is enabled and ROM 14 is disabled. The direction of data transfer will be from data bus 10 to data bus 11 so that the display controller internal data bus communicates directly with the CRTC controller data bus 11. During CRTC control register write operations (as distinguished from address write operations), once again the $\overline{W}$ will be low, but A0 will be high. In this instance, the EN input of buffer 16 is set high to disable buffer 16 and the 0E input of ROM 14 is set low to enable it. Thus the ROM can translate values received from the software to those required by the higher resolution display and place them on 6845 data bus 11.

Figure 2:
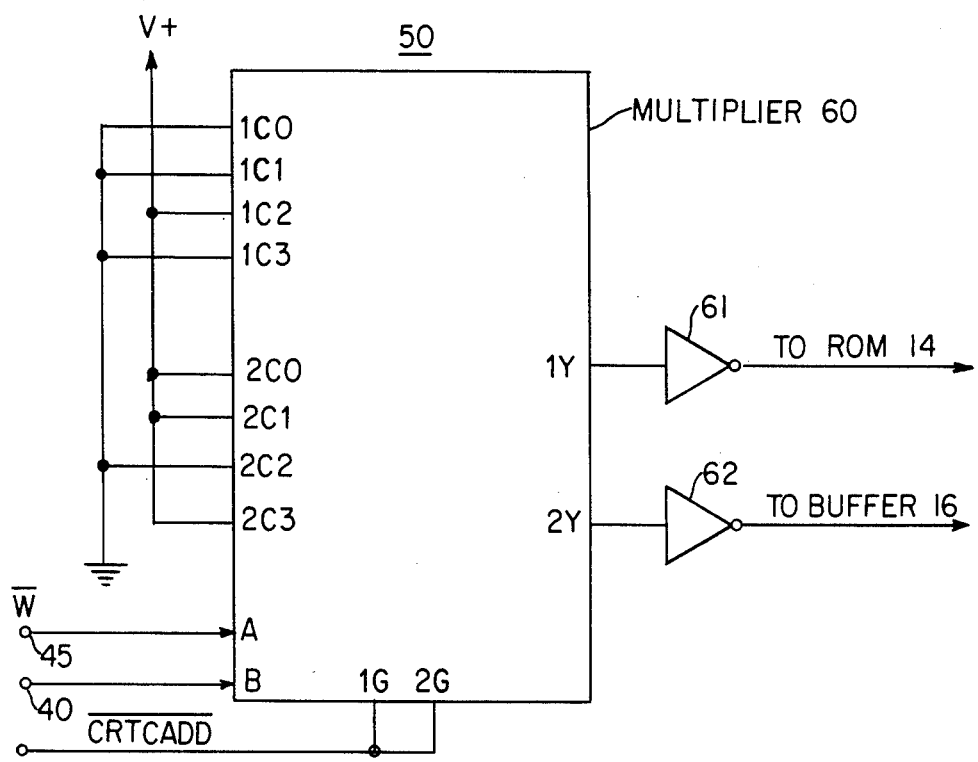
FIG. 2 is a diagram of a specific embodiment of control logic for use in the device according to the present invention.

These functions are summarized in table 2 and may be implemented by control logic 50 shown in FIG. 2. FIG. 2 shows a specific embodiment of control logic 50. In this embodiment, control logic 50 comprises a multiplexer 60 and inverters 61 and 62. The multiplexer may be of any type known in the art for example a 74LS352 which is manufactured by a number of semiconductor suppliers.

TABLE 2

| B(A0) | A($\overline{W}$) | OUTPUT TO ROM 14($\overline{1Y}$) | OUTPUT TO BUFFER 16($\overline{2Y}$) |
|---|---|---|---|
| 1 | 1 | 1 | 0 |
| 1 | 0 | 0 | 1 |
| 0 | 1 | 1 | 0 |
| 0 | 0 | 1 | 0 |

A multiplexer such as the 74LS352 is a dual 4-line to 1-line multiplexer. In operation, it transfers data selected from one of the four inputs 1C0 to 1C3 and present it to its 1Y output and correspondingly select data applied to one of the inputs 2C0–2C3 and applies to the output 2Y. The multiplexer includes an internal logic control determined by signal to the A and B terminals which functions to select a signal from one of the 1C0–1C3 and 2C0–2C3 input, and apply it to the 1Y and 2Y output terminals respectively. The 1G and 2G inputs receive the $\overline{CRTCADD}$ (CRT address) signal which is a strobe signal. With a multiplexer such as the 74LS352 and others, whenever the strobe terminals receive a high signal, the output will go low regardless of the data at data input 2C0–2C3 and regardless of the condition of the select inputs A and B. Thus, the multiplexer 60 is only enabled when the 1G and 2G signals are low. In the present invention, this will correspond to when the CRTC 20 is being addressed (that is when $\overline{CRTCADD}$=0).

Inputs 1C0, 1C1, 1C3 and 2C2 of multiplexer 60 are all tied to ground and thus have a logical 0 input applied to them. Inputs IC2, 2C0, 2C1 and 2C3 are all tied to the positive supply voltage, thus having a logical 1 applied to them. The signals are multiplexed in accordance with table 2. Thus, when the A0 signal is high and a read operation is indicated, multiplexer 60 provides a logical 0 signal corresponding to 1C3 at its 1Y output. This is in turn inverted by inverter 61 and disables ROM 14. It will also produce a signal equivalent to 2C3 at the 2Y output. This signal is a logical 1 which is in turn inverted by invertor 62 and applied to buffer 16 to enable buffer 16 and permitting the transfer of data between data bus 10 and data bus 11. Since the $\overline{W}$ signal is also applied directly to the direction (DIR) input of buffer 16, it permits the flow of data from data bus 11 to data bus 10 to complete the read operation.

In the instance where the A input is low (W=0) and the B input of the multiplexer is high (A0=1) a logical 1 output is supplied at the 1Y output which is inverted by inverter 61 where it is coupled to the OE input of ROM 14 which is thus enabled. The 2Y output of multiplexer 60 will receive a signal equivalent to 2C2 which is equal to 0. The signal is in turn inverted by invertor 62 to provide a logical 1 signal to buffer 16 at its EN input to disable it. The buffer 16 thus isolates data bus 10 from data bus 11.

In a third state, a logical 0 is applied to the B input of multiplexer 60 from the A0 signal and a logical 1 is applied to the A input corresponding to a read operation ($\overline{W}$=1). In this case, a logical 0 is presented to the 1Y output which is in turn inverted by invertor 61 to present a logical 1 to ROM 14. This disables ROM 14. At the same time a logical 1 is applied to output 2Y corresponding to the input at C1. This signal is in turn inverted by invertor 62 to enable buffer 16. Thus, it becomes possible to read from the data bus. Correspondingly, at this time, buffer 16 permits the transfer of data from data bus 11 to data bus 10 since the $\overline{W}$ signal is high.

Finally, in the last state corresponding to an address register call, the signal applied to the B input of multiplexer 60 (A0) is a logical 0 and the signal applied to the A input of multiplexer 60 ($\overline{W}$) is also logical 0. In this instance, the 1Y output takes on the value of the signal at C0 which in this case is equal to logical 0 and the 2Y output becomes equal to the signal at 2C0 which is equal to logical 1. The signals are in turn inverted respectively by invertors 61 and 62. Thus, ROM 14 is disabled and buffer 16 is enabled. Since the $\overline{W}$ signal is low, buffer 16 permits data to be transferred from data bus 10 to data bus 11. This corresponds to the situation where it is desired to write directly to the address register of CRTC 20. As stated at this time, it is desired that the convertor remain transparent so that the address received from the software can be applied directly to the controller.

Table 3 is a summary of possible values which may be placed into the ROM 14. The address has been broken down into the address for individual tables within the ROM as applied to terminals A8–A11 and to the specific data input from the software corresponding to the address as A0–A7. Reference to table 1 will show how the values may differ from those ordinarily used in the industry standard machine. For example, referring to address 03 for register R3 in the present invention, the value OC is selected regardless of the value typically used by the standard computer. In this case, it is ordinarily OA. This signal which as described previously corresponds to the horizontal sync width is generally independent of any software requirements.

TABLE 3

| A8–A11 | Address (A0–A7) | Value | Function |
|---|---|---|---|
| 00 | 0–55 | 39 | R0 40 × 25 |
|  | 56–7F | 73 | R0 80 × 25 |
|  | 80–FF | 0–7F | R0 TRANSPARENT |
| 01 | 100–1FF | 0–FF | R1 |
|  | 200–27F | 2–81 | R2 |
| 02 | 280–2FF | 0–7F | R2 |
| 03 | 300–3FF | 0C | R3 |
|  | 400–440 | 1A | R4 ALPHA |
|  | 441–47F | 6B | R4 GRAPHICS |
| 04 | 480–4FF | 0–7F | R4 TRANSPARENT |
|  | 500–57F | 0 | R5 |
| 05 | 580–5FF | 0–7F | R5 TRANSPARENT |
| 06 | 600–6FF | 0–FF | R6 |
|  | 700–740 | 19 | R7 ALPHA |
|  | 741–77F | 64 | R7 GRAPHICS |
| 07 | 780–7FF | 0–7F | R7 TRANSPARENT |
|  | 800–B02 | 00 | R8 |
|  | 803 | 03 | R8 (INTERLACED) |
| 08 | 804–87F | 00 | R8 |
|  | 880–BFF | 0–7F | R8 TRANSPARENT |
| 09 | 900–97F | 1–FF | R9 ((ADDR*2) + 1) |
|  | 980–9FF | 0–7F | R9 TRANSPARENT |
|  | A00–A7F | * | R10 (* IF ADDRESS MOD 20 < 10 THEN VALUE = (ADDRESS − A00) + ADDRESS MOD 20 ELSE VALUE = (ADDRESS − ADDRESS MOD 20) + 10)) |
| 0A | AB0–AFF | 0–7F | R10 TRANSPARENT |
| 0B | B00–B7F | 0–FE | R11 (STEP 2) |

TABLE 3-continued

| A8-A11 | Address (A0-A7) | Value | Function |
|---|---|---|---|
| | BB0-BFF | 0-7F | R11 TRANSPARENT |
| 0C-0F | C00-FFF | ** | R12-15 |
| | | | (** VALUE = ADDRESS MOD 100) |

The present invention can also be completely bypassed when desired. For example, when used with software which writes values to the CRTC 20, but which has been developed specifically for a microcomputer utilizing the higher resolution display, the ROM can be made transparent by adding a value $N+R_0$ to the control register values. These transparent values are noted on table 3 as being transparent. It will be noted that in this particular case, the binary address of the transparent values all have a most significant bit equal to 1. This provides a simple and convenient method for a software programmer to bypass the ROM 14.

The present invention also permits changes in the CRT raster rate. For example, in the previously discussed IBM PC a 15.75 kilohertz scan rate is utilized which corresponds to a similar scan rate used in commercial television broadcasts and receivers. In one computer developed using the present invention a scan rate of 26 kilohertz is used. Further, it was found that the flyback period could be shortened to therefore increase the useful time of the scan. Were software adapted to the IBM PC scan rate of 15.75 kilohertz utilized without conversion in such a computer, the display would be completely garbled.

Although the invention has been described for use in adapting software designed for a low resolution CRT to be used with a microcomputer utilizing a high resolution CRT, it may be used in any situation where a computer demands different parameters for its display than was originally contemplated by the software being used with the computer. Thus, the software can remain compatible and the microcomputer will automatically adjust the software to the requirements of its particular display.

What is claimed is:

1. In an improved computer display adapted to be controlled by programmable display controller means, said display having a computer data bus for providing data to program said controller means with display parameters required by said display, and a controller data bus for transferring said data to said controller means, said display having predetermined characteristics requiring programming of said controller means with parameters defined by a first value of said data, said computer data bus being adapted to supply data having a second value defined for programming the controller means for another display having characteristics different from said predetermined characteristics, wherein the improvement includes a device for converting data having said second value into data having said first value, said device comprising:
   memory means interposed between said computer data bus and said controller data bus and being connected to be addressed by data having said second value for providing to said controller data bus data having said first value; and
   control logic means connected to said memory means for selectively enabling and disabling said memory means, whereby said controller means is always programmed according to said first value.

2. In an improved computer display adapted to be controlled by programmable display controller means, said display having a computer data bus for providing a plurality of data to program said controller means, said plurality of data each including a first portion for selecting an address within said controller means and a second portion for programming said controller means with a parameter associated with said address, and a controller data bus for transferring said data to said controller means, said display having predetermined characteristics requiring said controller means to be programmed with parameters defined by a first value of said second portion, said computer data bus being adapted to supply data including a second portion having a second value defined for programming the controller means for another display having characteristics different from said predetermined characteristics, the improvement comprising:
   buffer means interposed between said computer data bus and said controller data bus for selectively isolating and directly coupling said data buses;
   storing means connected to said computer data bus for temporarily storing the first portion of said data,
   memory means jointly addressable by the first portion of said data stored by said storing means and by the second portion of said data having said second value for providing to said controller data bus a second portion of said data having said first value; and
   control logic means connected to said memory means and said buffer means for selectively enabling said memory means and disabling said buffer means, whereby said controller means is always programmed according to said first value.

3. A device according to claim 2, wherein said memory means includes first and second groups of address lines, the first group of address lines receiving the first portion of data stored in said storing means and the second group of address lines being coupled to said computer data bus for receiving said second portion of data.

4. The device according to claim 3, wherein said first portion of data and second portion of data are sequentially supplied by said computer data bus.

5. The apparatus according to claim 4, wherein:
   said first portion of data is loaded by said storing means and stored therein for application to said memory means, while said second portion of data is received by said memory means from said computer data bus; and
   said memory means includes data organized into a group of tables and lines of data therein, said tables selected by said first group of data received from said storing means and said lines in said tables being selected by said second portion of data received by said memory means from said computer data bus.

6. The apparatus according to claim 5, wherein said display controller means is a CRT controller.

7. The apparatus according to claim 6, wherein said CRT controller comprises:
   register select means adapted to receive a register select signal which is either a logical 0 signal or a logical 1 signal; and
   wherein when said register select means receives a logical 0 signal said first portion of data is received on said controller data bus to select a register for controlling display parameters of said controller, and when a logical 1 is received at said register select means said second portion of data having said first value is received on said controller data bus and is applied to said control register selected according to said first portion of data.

8. The device according to claim 6 wherein said buffer means is a bidirectional buffer for selectively permitting the flow of data from said CRT controller to said computer data bus and for permitting the flow of data from said computer data bus to said controller data bus.

9. The apparatus according to claim 7 wherein said storing means stores said first portion of data when said register select signal received at said register select means is equal to logical 0.

10. The device according to claim 9 wherein:
said control logic means includes means for receiving a write signal and said register select signal, said control logic means having a first output connected to said buffer means and a second output connected to said memory means;
wherein, when said write signal is in a first state and said register select signal is in either a first or second state said buffer means is enabled and said memory means is disabled;
wherein, when said write signal is in a second state and said register select signal is in a second state said buffer means is enabled and said memory means is disabled; and
wherein, when said write signal is in a second state and said register select signal is in a first state said buffer is disabled and said memory means is enabled.

11. The device according to claim 10, wherein said control logic means comprises multiplexing means having a plurality of inputs coupled to fixed logical zero and fixed logical 1 signals and connected to said memory means and said buffer means, by two corresponding outputs for selecting said fixed logical signals at said multiplexer inputs for coupling said multiplexer selected signals to said buffer and said memory means for disabling and enabling them.

12. A device according to claim 10, wherein the direction of the bidirectional buffer is controlled by said write signal.

* * * * *